(12) United States Patent
Guimberteau et al.

(10) Patent No.: US 8,895,063 B2
(45) Date of Patent: Nov. 25, 2014

(54) ORAL DOSAGE FORM COMPRISING AN ANTIMISUSE SYSTEM

(75) Inventors: Florence Guimberteau, Montussan (FR); Frederic Dargelas, Pessac (FR); Gérard Soula, Meyzieu (FR); Rémi Soula, Lyons (FR)

(73) Assignee: Flamel Technologies, Venissieux (FR)

( * ) Notice: Subject to any disclaimer, the term of this patent is extended or adjusted under 35 U.S.C. 154(b) by 276 days.

(21) Appl. No.: 11/651,577

(22) Filed: Jan. 10, 2007

(65) Prior Publication Data

US 2008/0008659 A1 Jan. 10, 2008

Related U.S. Application Data

(63) Continuation of application No. 11/439,247, filed on May 24, 2006.

(51) Int. Cl.
| | | |
|---|---|---|
| *A61K 8/20* | (2006.01) | |
| *A61K 9/50* | (2006.01) | |
| *A61K 45/06* | (2006.01) | |
| *A61K 33/30* | (2006.01) | |
| *A61K 33/26* | (2006.01) | |
| *A61K 33/06* | (2006.01) | |
| A61K 9/48 | (2006.01) | |

(52) U.S. Cl.
CPC ............ *A61K 9/5047* (2013.01); *A61K 9/4825* (2013.01); *A61K 9/5084* (2013.01); *A61K 45/06* (2013.01); *A61K 33/30* (2013.01); *A61K 9/5078* (2013.01); *A61K 33/26* (2013.01); *A61K 33/06* (2013.01)
USPC ........................................................ 424/464

(58) Field of Classification Search
None
See application file for complete search history.

(56) References Cited

U.S. PATENT DOCUMENTS

| | | | |
|---|---|---|---|
| 5,603,957 A * | 2/1997 | Burguiere et al. ............ 424/489 |
| 5,780,055 A | 7/1998 | Habib et al. |
| 6,264,983 B1 * | 7/2001 | Upadhyay ..................... 424/464 |
| 6,696,088 B2 | 2/2004 | Oshlack et al. |
| 2003/0068371 A1 | 4/2003 | Oshlack et al. |
| 2003/0068392 A1 | 4/2003 | Sackler |
| 2003/0083286 A1* | 5/2003 | Teng et al. ....................... 514/44 |
| 2003/0118641 A1* | 6/2003 | Maloney et al. ............... 424/465 |
| 2003/0224051 A1 | 12/2003 | Fink et al. |
| 2004/0022849 A1 | 2/2004 | Castan et al. |
| 2004/0126428 A1 | 7/2004 | Hughes et al. |

(Continued)

FOREIGN PATENT DOCUMENTS

| | | | |
|---|---|---|---|
| CA | 2459976 A1 | 4/2003 |
| CA | 2499994 A1 | 4/2004 |

(Continued)

*Primary Examiner* — Paul Dickinson
(74) *Attorney, Agent, or Firm* — Porzio, Bromberg & Newman P.C.

(57) ABSTRACT

An oral solid dosage form containing one or several active principle(s) having analgesic properties, the composition of said dosage form being such that it prevents the misuse of said dosage form through the liquid extraction of the active principle(s) contained therein, using commonly available solvents.

Said oral solid dosage form containing at least one salt of at least one analgesic active principle, and an anti-misuse system comprising at least one quenching agent, said quenching agent being suitable for inducing complexation of said analgesic active principle salt when the analgesic active principle salt is improperly extracted, notably by a drug abuser, in vitro in solution from said oral solid dosage form.

42 Claims, 2 Drawing Sheets

(56) References Cited

U.S. PATENT DOCUMENTS

| | | |
|---|---|---|
| 2004/0228924 A1* | 11/2004 | Oshlack et al. ............... 424/489 |
| 2005/0031546 A1 | 2/2005 | Bartholomaus et al. |
| 2005/0106249 A1* | 5/2005 | Hwang et al. ................. 424/469 |
| 2005/0163856 A1 | 7/2005 | Maloney et al. |
| 2005/0214223 A1 | 9/2005 | Bartholomaues et al. |
| 2005/0266078 A1 | 12/2005 | Jorda et al. |
| 2005/0281748 A1* | 12/2005 | Hirsh et al. .................. 424/10.1 |
| 2007/0264326 A1 | 11/2007 | Guimberteau et al. |
| 2009/0041838 A1 | 2/2009 | Guimberteau et al. |

FOREIGN PATENT DOCUMENTS

| | | |
|---|---|---|
| EP | 0709087 | 5/1996 |
| EP | 1293209 | 3/2003 |
| FR | 2811571 A1 | 1/2002 |
| WO | WO 0108661 | 2/2001 |
| WO | WO-03/013467 A1 | 2/2003 |
| WO | WO-03013479 | 2/2003 |
| WO | WO-03030878 | 4/2003 |
| WO | WO-03/077888 A2 | 9/2003 |
| WO | WO-03/082204 A2 | 10/2003 |
| WO | WO 03103538 | 12/2003 |
| WO | WO 2004004693 | 1/2004 |
| WO | WO-2004010983 | 2/2004 |
| WO | WO-2004010984 | 2/2004 |
| WO | WO-2004/026262 A2 | 4/2004 |
| WO | WO 2004037259 | 5/2004 |
| WO | WO-2004/052346 A1 | 6/2004 |
| WO | WO-2004/054542 A2 | 7/2004 |
| WO | WO 2005163314 | 2/2005 |
| WO | WO-2005/079760 A1 | 9/2005 |
| WO | WO-2006/056712 A1 | 6/2006 |
| WO | WO-2006/056713 A1 | 6/2006 |
| WO | WO-2006/089843 | 8/2006 |
| WO | WO 2006/125819 A2 | 11/2006 |

* cited by examiner

ORAL DOSAGE FORM COMPRISING AN ANTIMISUSE SYSTEM

CROSS-REFERENCE TO RELATED APPLICATIONS

This application is a continuation of U.S. application Ser. No. 11/439,247 filed May 24, 2006, currently pending, which claims benefit of PCT/EP2005/012721, filed Jun. 13, 2005, currently pending. The contents of which are incorporated herein in their entirety.

FIELD OF THE INVENTION

The present invention relates to an oral solid dosage forms containing one or several active principle(s) having analgesic properties, the composition of said dosage form being such that it prevents the intentional or unintentional misuse of said dosage form through the liquid extraction of the active principle(s) contained therein, using commonly available solvents.

More specifically, the analgesic active principle (AAP) is present in the oral solid dosage form is a pharmaceutically acceptable salt. In the present disclosure, the mention analgesic active principle means a pharmaceutically acceptable salt of analgesic active principle.

BACKGROUND OF THE INVENTION

Analgesics, and more particularly opioid or morphine derivatives, are often misused. Such misuse can be intentional or unintentional consumption of a solid oral drug containing an analgesic active principle, for a purpose other than that which is officially approved by the competent health authorities. This is a very complex and difficult problem to solve. The reason is that drug abuses and unfortunately now even teenagers have found way to recover the drug from tablets quite easily.

For example, today, teenagers prepare for parties on Saturday, a cocktail of vodka with Oxycodon that they extract easily from tablets, with water or alcohol. The process consists in crushing the tablet and pouring the powder into a glass of vodka or water and then, to wait long enough to extract almost completely all the morphines derivative. They use to do the preparation of the drug before they take it. This practice is widespread in US but also in Europe. This is becoming a real social concern addressed by social agencies but also by the Food and Drug Administration in US and European Agencies, who wish that dosage forms preventing misuse be developed.

There are other ways to misuse the type of opoïd such as extracting the drug as described above and make an intravenous injection or dry the drug in order to obtain a powder which can be inhaled.

There is a prior art describing different solution to avoid the misusage of opioids contained into a delivery systems.

Our understanding is that patent application US-A-2003/0224051 describes osmotic delivery dosage forms for the modified release of oxycodone. The dosage form comprises an oxycodone core or acceptable salts thereof, a semi-permeable membrane at least partially surrounding the core, an exit orifice through the membrane allowing the release of oxycodone. This type of tablet allows an easy extraction by water for example after 12 hours or more and consequently does not provide i.a. a satisfactory solution against misuse.

Another way to avoid misuse of an opioid is to combine the opioid with its antagonist such as naltrexone. Our understanding is that patent application WO-A-03/013479 patent describes an oral dosage form comprising a therapeutically effective amount of an opioid analgesic; an opioid antagonist (naltrexone); and a bittering agent. When the drug abuser crushes the tablet, the opioid and its antagonist are released and the opioid effect is neutralised.

This system does not prevent i.a. extraction by water because, without crushing, the opioid can be extracted, contrary to naltrexone.

Our understanding is that published European patent application EP-A-1293209 describes a solid oral pharmaceutical dosage form with reduced potential for drug abuse. The oral dosage form of the invention is a sustained release dosage form based on an ion exchange resin which contains an opioid derivative. However, this dosage form does not prevent solvent extraction with an extraction time longer than the normal release time of the drug. If said oral dosage form is left in a glass of water during 24 hours, most of the drug will be extracted.

As can be seen from the foregoing presentation of the prior art, different solutions are provided to prevent misuse of pharmaceutical opioids in modified release solid dosage forms.

However, our understanding is that none of the solutions can prevent i.a. the extraction by water, alcohol or any other type of drinkable solvent.

OBJECTIVES OF THE INVENTION

In these circumstances, one of the main objects of the instant invention is to fill in the prior art.

Thus, according to one aspect of the invention it is an object of the invention to provide a new solid oral analgesic medicine/dosage form, allowing for the prevention of oral misuse after liquid extraction such as a "long" liquid extraction of the analgesic active principle, in one aspect without resorting to antagonists of the analgesic active principle.

By "long liquid extraction", it is meant that the liquid extraction is planned by the drug abuser to last longer than 10 minutes.

According to further aspects of the invention, it is an objective of the invention to provide a solid oral dosage form containing an analgesic active principle, said dosage form having the following features:

Under normal prescribed condition of administration, the dosage form should have the desired therapeutic effect, for example during 12 hours or 24 hours;

Under any attempt of improper extraction of the analgesic by a misuser, the oral dosage form will not be able to provide fast absorption of the analgesic into the blood circulation. Another objective of the invention is to provide a new solid oral dosage form that prevents misuse by a long liquid extraction as well as a brief liquid extraction and/or by crushing.

Another objective of the invention is to provide a new solid oral analgesic dosage form:

which can be administered easily to patients having difficulties to swallow large tablets, among which infants, children and the elderly;

which permits the association of several analgesic active principles, or even other nonanalgesic active principles, in a single dosage form, even when said active principles are not compatible with one another and/or when said active principles have distinct release kinetics;

which permits the provision of an oral pharmaceutical dosage form of analgesic active principle, or even other nonanalgesic active principles, which is administered once a day or several times a day, it being possible to adjust easily and independently the release rate and the release time of said active principles.

A further object of the invention is to provide an oral pharmaceutical dosage form of analgesic active principle, the in vitro dissolution profile of which is independent from the dose of analgesic active principle.

Another object of the invention is to provide an oral pharmaceutical dosage form of analgesic active principle, which can be administered e.g. once a day and which limits the risks of tissue damage due to local over-concentration of said active principle.

Still a further object of the invention is to provide an oral pharmaceutical dosage form of analgesic active principle which can be formulated into different galenical forms, such as tablets, powders, sachets, capsules and the like.

It is an object of the invention to provide a new solid oral drug that prevents misuse while not compromising the treatment of a patient who conforms to a regular therapy, in particular as regards this patient's needs in terms of dose of active principle.

Yet another objective of the invention is to provide a new solid oral drug that prevents misuse, which is easily prepared and the preparation process of which does not unduly increase its manufacturing cost.

SUMMARY OF THE INVENTION

To achieve these objectives, it is to the inventor's credit to have discovered means suitable to quench an analgesic active principle such as an opioid when it is extracted from the dosage form for misuse purpose.
According to one aspect of the invention the dosage form has the following features:

Under normal prescribed condition of administration, the dosage form has the desired therapeutic effect for example during 12 hours or 24 hours;

Under any attempt to extract the analgesic, with or without crushing, the analgesic is quenched in vitro by a safe and even generally recognized as safe substance (GRASS) in order to avoid its fast absorption into the blood circulation and hence neutralize the fast action of the drug;

The quenching agent forms a complex which is poorly soluble in water at any physiological pH from the stomach to the colon.

According to this aspect the invention provides a solid oral dosage form that contains at least one quenching agent, this quenching agent being suitable for inducing complexation of the analgesic active principle when the analgesic salt is released in solution from the solid oral dosage form.
Within the meaning of this invention a "quenching agent" is an agent that is present in the dosage form in a free form, i.e. in a non-complexed form, "non-complexed" meaning that no complex or chemical interaction of the quenching agent with the analgesic active principle exists within the dosage form. Only when the analgesic active agent and the quenching agent are combined in a solvent, e.g. in case of an illicit extraction attempt, the quenching agent is suitable for inducing complexation or chemical interaction with the analgesic active principle in a common solvent as described herein. The quenching agent is considered to be "suitable to induce complexation" of the analgesic active principle within the meaning of the present invention, when the quenching agent is suitable to induce said complexation (of the analgesic active principle) in at least one common solvent selected from the group of water and aqueous solvent systems, such as water-ethanol mixtures, alcohol, alcoholic beverages, sodas, vinegar, and/or hydrogen peroxide, and mixtures thereof. Advantageously, the quenching agent is suitable to induce said complexation (of the analgesic active principle salt) in more than one of these common solvents.

A further aspect of the invention is to provide a solid oral dosage form wherein the quenching agent cannot be removed from the system.

In other words, according to one aspect, the invention relates to an oral solid dosage form containing at least one salt of at least one analgesic active principle, and an anti-misuse system comprising at least one quenching agent, said quenching agent being suitable for inducing complexation of said analgesic active principle salt when the analgesic active principle salt is improperly extracted, notably by a drug abuser, in vitro in solution from said oral solid dosage form.

This solution was not self evident as it was necessary to define an efficient but a safe and generally recognized as safe substance quenching additive in the case where the drug abuser intends to extract the drug. At the same time, the system should permit to release the drug in the body following the targeted pharmacokinetic profile. In other words, the desired pharmacological effect of the analgesic active principle is not impaired by the quenching agent when the dosage form is not misused. This new system will be called hereafter "Trigger Lock" system.

The invention provides a solid dosage form comprising an encapsulated analgesic active principle in a salt form and at least one quenching agent such as e.g. an encapsulated quenching agent. In case of an encapsulated quenching agent said quenching agent is released at such speed that it can complex the analgesic active agent principle when it is itself released by extraction from the oral solid dosage form. The quenching takes place when the quenching agent and the analgesic (e.g. for example the opioid) have been extracted in vitro by the solvent, forming a complex poorly soluble in the stomach medium. Thus, the concentration of analgesic active principle remaining in solution is low after extraction, i.e. the amount of active principle remaining in solution is insufficient to provide the effects desired by the drug abuser.

Alternatively, the quenching agent can be an ion exchange resin, in which case the analgesic active principle does not form a complex with the ion exchange resin when properly used. For instance, the quenching agent can be a salt of an anionic exchange resin, the cation of which is $H^+$, a metallic cation and/or $NH_4^+$. More precisely, according to this aspect of the invention said ion exchange resin is comprised in a first phase separate from a second phase, said second phase comprising said analgesic active principle.

According to one aspect the dosage form comprises microparticles of analgesic active principle and microparticles of quenching agent such as microparticles of ion exchange resin, said microparticles have the same size distribution, the same density and are not sievable, i.e. not easily separable.

These last characteristics of the Trigger Lock system ensure that ingestion of the complex does not lead to any fast regeneration and/or fast extraction of the analgesic active principle once ingested by the drug abuser. Thus, the massive absorption of the analgesic, as desired by the drug abuser, and the consequent massive blood concentration of analgesic, is avoided.

According to another aspect of the invention, the analgesic active principle and the quenching agent are both in a modified release form. For example both the analgesic and the quenching agent could be released according to a sustained release kinetics. Thus, it is impossible, or at least very difficult, to extract separately in vitro the analgesic active principle and the quencher. In other words, the analgesic active principle and quenching agent are necessarily extracted together and thus form a poorly soluble complex.

When the dosage form according to the instant invention is administered orally in accordance with the prescriptions of the health authorities, said dosage form releases slowly both the analgesic active principle and the quenching agent in the gastric fluids where they are both diluted, so that no complexation occurs. Then, the analgesic active principle can be correctly bio-absorbed.

According to one aspect of the invention the dosage forms contain a plurality of microparticles.

It is also the inventors' credit to have designed a microparticulate system comprises a first microparticles population with the drug and a second microparticles population with the quenching agent. Both microparticles populations comprise a plurality of microparticles such as more than 1,000 microparticles. This is believed to permit a fast dispersion of all the microparticles, thereby avoiding interaction of the quenching agent and the analgesic active principle in the body.

Without this being limiting, it is preferred according to the invention that the coated microparticles of PA have a mean diameter smaller than or equal to 1000 µm, preferably comprising between 50 and 800 µm and, still preferably, comprising between 100 and 600 µm, and still better between 100 and 300 µm.

According to one aspect of the invention it is also one element of the invention to propose a delayed release for the quencher in order to have enough time in the body to disperse the microparticles before the quencher neutralizes the analgesic active principle.

According to a further aspect of the invention, after administration of the dosage form according to the prescriptions of the health authorities, the analgesic is slowly released but the release of the quencher starts only after a lag time of typically 0.25 to 3 hours. During this lag time, the microparticles of analgesic and the microparticles containing the quencher are broadly dispersed in the gastro-intestinal tract and the quencher can no longer neutralize the analgesic.

Such a modified release of the quencher in the stomach, optionally after a modified lag time is conveniently obtained by coating the microparticles containing the quenching agent with a film coating, the composition of which is detailed hereinbelow. According to an even further aspect of the invention the microparticulate dosage forms are less easy to crush or to chew.

Preferably, the complex of the quenching agent and the analgesic is poorly soluble in common solvents such as a water-ethanol mixture. In other words, the concentration of analgesic active principle remaining in solution is low, i.e. the amount of analgesic active principle in solution is not sufficient to produce the effect desired by the drug abuser.

Preferably, the novel oral solid dosage form of the instant invention does not contain antagonists of the analgesic active principle.

DETAILED DESCRIPTION OF THE INVENTION

The concept at the root of the invention is to include within a solid oral dosage form a quenching agent (quencher), namely a salt. This salt comprises an ion which has a polarity opposite to that of the analgesic active principle in solution. Preferably it is an organic ion such as an ion exchange resin. It can also be a metallic ion.

When in solution, said ion replaces the initial counter-ion of the analgesic active principle, leading to a substantially insoluble complex. As a consequence, the analgesic active principle is no longer free in solution. By "no longer free in solution" or "low concentration" is meant that the concentration of analgesic active principle remaining in solution is below the concentration desired by the drug abuser, or it is not sufficient to produce the desired effect by the drug abuser.

On the contrary, when the oral dosage form is administered according to the regimen prescribed by the health authorities, the dilution of the quenching agents in the gastrointestinal tract fluids is sufficient to prevent the reaction of the quenching agent with the analgesic active principle. Thus the therapeutic effect of the analgesic active principle is met.

Preferably, the active principles considered in the instant disclosure are analgesic active principles. Non-analgesic active principles can also be included. In this specification, the mention of "an active principle" or "the active principle" includes both the singular and the plural, and the mixture of different active principles.

The same convention applies to the mention of "a quenching agent" or "the quenching agent". Both include the singular, the plural and mixtures of different quenching agents.

By "oral dosage form" is meant in this disclosure any dosage form wherein the active principle is comprised in tablets (monolithic dosage form) or in microparticles (multi-microparticulate dosage form). These dosage forms can be immediate release dosage forms or modified release dosage forms. In the latter case, the tablet or the microparticle core containing the active principle can be coated with a polymer coating that controls the release rate of the active principle after oral administration.

By "immediate release dosage form" is meant the release by a dosage form of the major part of the active principle dose in a short time, for instance, 70% of the active principle are released in 1 hour, preferably in 30 min., at any pH between 1.4 and 6.8, during an in vitro dissolution test.

By "modified release dosage form" is meant any dosage form wherein at least a fraction of the active principle is released at a lower rate than in an immediate release dosage form. This fraction can be comprised between 1 and 100%, preferably, between 10 and 100%, and even more preferably between 30 and 100%. A modified release dosage form can comprise an immediate release phase and a sustained or delayed release phase. Modified release dosage forms are well known in the art, see for instance Remington: *The science and practice of pharmacy,* 19éme edition, Mack publishing Co. Pennsylvania, USA. Modified release comprises, notably, sustained release, delayed release, and pulsed release.

By "long liquid extraction", it is meant that the liquid extraction is planned by the drug abuser to last longer than 10 minutes.

By "household solvent" or "common solvent", it is meant a liquid that can usually be found in a household and that can be used as an extraction solvent. For instance, it designates water and aqueous solvent systems such as water-ethanol mixtures, alcohol, alcoholic beverages, sodas, vinegar, and/or hydrogen peroxide, and mixtures thereof. Water-ethanol mixtures are encompassed as well.

Other definitions are given in the instant disclosure.

The quenching agents used to trap the analgesic active principle are innocuous to the regular user. These quenching agents are pharmacologically inert, approved by the Pharmacopoeia and health authorities in charge of market approval of drugs. The quenching agent is selected so that, during an attempt to extract the active principle in an aqueous solution or an alcoholic aqueous solution, said quenching agent forms a low solubility complex with the active principle in solution.

Preferably, the quenching agent comprises a salt, said salt containing ions which form a complex with said analgesic active principle in solution. Said ions are preferably organic ions that have a polarity opposite to that of the analgesic active principle salt in solution. When the analgesic active principle salt is in the form of an anion in solution, the quenching agent comprises an organic cation, a metallic cation or a mixture thereof. Similarly, when the analgesic active principle salt is in the form of a cation in solution, the quenching agent comprises an organic anion.

For example, the following salts containing an organic anion can be listed:
  organic anionic salts, such as sodium dodecyl sulfate or sodium docusate;
  anionic polymers, such as (meth)acrylic copolymers (for instance Eudragit® S et L), crosslinked acrylic polyacids (for instance, Carbopol), cellulose carboxymethylcellulose and its derivates, crosslinked carboxymethylcellulose and its derivates and other polysaccharides (for instance, alginate, xanthane or arabic gum), alginate (sulfonate)propylene glycol;
  mono- or polyvalent salts, such as glucuronates, citrates, acetates, carbonates, gluconates, succinates, phosphates, glycerophosphates, lactates, trisilicates, fumarates, adipates, benzoates, salicylates, tartrates, sulfonamides, acesulfames;
  saponified fatty acids, such as the salts of acetic acid, succinic acid, citric acid, stearic acid, palmitic acid, and self emulsifying glyceryl mono-oleates;
  polyamino acid, proteins or peptides, such as albumins, caseins, globulins and enzymes;
  and mixtures thereof.

In another embodiment, said ion having a polarity opposite to that of the analgesic active principle salt in solution, is a metallic cation, an organic cation, or a mixture thereof. For example, the following salts containing an organic cation or a metallic cation can be listed:
  metallic cationic salts for example of Ca, Fe, Mg, Zn, in the form of acesulfames, acetates, adipates, benzoates, carbonates, chlorides, citrates, fluorides, fumarates, gluconates, glucuronates, glycerophosphates, hydroxides, iodates, iodides, lactates, oxides, phosphates, trisilicates, phosphates, salicylates, succinates, sulfonamides, tartrates salts;
  organic cationic salts, such as quaternary ammonium salts, in particular trimethyl tetradecyl ammonium bromide or benzethonium chloride;
  cationic polymers, such as chitosan and (meth)acrylic copolymers (for instance, Eudragit® RS, RL ou E);
  polyamino acid, proteins or peptides;
  and mixtures thereof.

The quenching agent can be an anionic exchange resin, in which case the analgesic active principle does not form a complex with the ion exchange resin. For instance, the quenching agent can be a salt of an anionic exchange resin, the cation of which is $H^+$, a metallic cation and/or $NH_4^+$. More precisely, said ion exchange resin is comprised in a first phase separate from a second phase, said second phase comprising said analgesic active principle.

The quenching agent Q can be an ion exchange resin, preferably a strong acid cation exchange resin where the AP is cationic, or a strong alcali anion exchange resin where the AP is anionic. Preferably, such an ion exchange resin is contained in a first phase distinct from a second phase, said second phase containing the AP.

In an embodiment of the invention, the quenching agent is a strong acid cation exchange resin, derived for example from a sulphonated copolymer of styrene and divinylbenzene, such as Amberlite® IRP69, Amberlite® IR69F, Amberlite® 200, Amberlite® 200C, from Rohm & Haas, or Dowex® 88, from Dow, and the like.

In a further embodiment of the invention, the quenching agent is a strong alcali anion exchange resin, derived for example from copolymers of styrene and divinylbenzene with quaternary ammonium functionality, such as Duolite® AP143, Amberlite® IRA958, Amberlite® IRP67, from Rohm & Hass, or Dowex® 22, from Dow.

According to one embodiment the quenching agent is an ion exchange resin and the quenching agent is present in a first phase separate from at least a second phase, said at least second phase comprising the PA salt. For instance, the first phase comprises microparticles comprising the quenching agent, separate from the second phase comprising microparticles comprising the PA salt. The microparticles comprising the PA salt and microparticles comprising the quenching agent may be in such a form where they have similar size distributions, similar densities and are not sievable.

According to one embodiment the quenching agent is an ion exchange resin and the quenching agent is present in a first phase separate from at least a second phase, said at least second phase comprising the PA salt. For instance, the first phase comprises microparticles comprising the quenching agent, separate from the second phase comprising microparticles comprising the PA salt. The microparticles comprising the PA salt and microparticles comprising the quenching agent may be in such a form where they have the same size distribution, the same density and are not sievable.

In one embodiment of the invention, the quenching agent Q is chosen from the group consisting of:
  anionic organic salts, such as sodium dodecyl sulfate or sodium docusate;
  cationic organic salts, such as quaternary ammonium salts, in particular trimethyl tetradecyl ammonium bromide or benzethonium chloride;
  strong acid cation exchange resins, of strong alcali anion exchange resins, depending on the AP polarity.

In another embodiment of the invention, the quenching agent Q is chosen from the group consisting of:
  strong acid cation exchange resins, such as Amberlite® IRP69, Amberlite® IR69F, Amberlite® 200, Amberlite® 200C, from Rohm & Haas, or Dowex® 88, from Dow, and the like, and mixtures thereof, where the AP is cationic;
  strong alcali anion exchange resins, such as Duolite® AP143, Amberlite® IRA958, Amberlite® IRP67, from Rohm & Hass, or Dowex® 22, from Dow, and mixtures thereof, where the AP is anionic.

The amount of quenching agent is adapted by the skilled man in the art, by computing the stoechiometric amount in terms of ionic charge, necessary to trap all or part of the dose of active principle contained in the dosage form. The amount must be at least sufficient to complex—in case of an illicit extraction attempt—the active principle to such an extent that the abuser does not achieve the desired high with the remaining active principle in solution. Preferably the amount is at least sufficient to complex all of the contained active agent PA in the dosage form.

The quenching agent is selected in view of the chemical properties of the active principle it aims, in particular its ionic form in solution.

For the liquid extraction of the analgesic active principle, the dosage form containing the active principle is generally placed into an extraction solvent, such as a household liquid (water, organic solvents, sodas, alcoholic beverages) for a time period longer than 10 minutes.

Preferably, the dosage form according to the invention does not contain an active principle that is an antagonist to the analgesic active principle, particularly in the case of an opioid agonist.

Preferably, the dosage form according to the invention comprises modified release units of said analgesic active principle and modified release units of said quenching agent. For instance, said modified release units comprise microparticles selected from the group comprising: sustained release microparticles, delayed release microparticles, pulsed release microparticles, and mixtures thereof.

A preferred embodiment is a multimicroparticulate dosage form. It is preferred that, when the dosage form comprises microparticles of analgesic active principle and microparticles of quenching agent, said microparticles have the same size distribution, the same density and are not sievable.

Said dosage form can also be a monolithic dosage form.

According to a preferred embodiment, the quencher contained in the oral solid dosage form of the invention is released following a modified release kinetic. Preferably, the quencher is contained in film coated microparticles, and most preferably, in microparticles coated with the same film coating as that used to coat the microparticles containing the analgesic active principle.

According to a preferred embodiment, the dosage form comprises a further antimisuse agent. Said further antimisuse agent aims at preventing drug abuse by injection, after a possible crushing and liquid extraction. In an additional embodiment, said further antimisuse agents are provided to prevent drug abuse by inhalation, after a possible crushing and liquid extraction. Therefor, said further antimisuse agent comprises an anti-crushing agent (a) and/or a viscosity agent (b).

Preferably, said anti-crushing agent (a) comprises:
a protective over-coating on said microparticles, said over-coating having at least one of the following features:
  viscoelastic properties, to absorb the energy dissipated during crushing;
  a low cohesivity, to favor breaking of the over-coating rather than breaking of the microparticles during crushing;
  a low surface energy, to favor gliding of the microparticles one on the other during crushing;
  an ability to form a paste under high shear,
and/or free additives, i.e. additives that are not contained in nor borne over microparticles, said additives being suitable to impair, or even to prevent completely, the crushing of the pharmaceutical dosage form containing said analgesic active principle.

In the case where an over-coating is provided to protect the dosage form, such as microparticles, the over-coating is prepared so that a non-immediate release of the analgesic active principle takes place even after the dosage form has been crushed.

More precisely, the over-coating of the dosage form comprises:
(i) at least one film forming polymer insuring the cohesion of the over-coating;
and at least one of the following compounds:
(ii) a lubricant/lump agent
(iii) a viscoelastic compound
(iv) a plasticizer.

In practice, said film-forming polymer (i) is selected from the group comprising cellulose derivatives, acrylic polymers and mixtures thereof.

Said lubricant/lump agent (ii) is selected from the group comprising:
stearic acid, stearates, preferably calcium stearate, zinc stearate or magnesium stearate,
magnesium oxide,
poloxamers,
sodium benzoate,
anionic, cationic or non-ionic surfactants,
starch, preferably corn starch,
talc,
colloïdal silica,
waxes, preferably hydrogenated vegetable oils, and more preferably: cotton hydrogenated oils, soybean hydrogenated oils, palm hydrogenated oils, glycerol behenate, castor hydrogenated oils, tristearines, tripalmitines, trimyristines, yellow wax, white wax, hard fat, dairy anhydrous fat, lanolins, glycerol palmitostearate, glycerol stearates, lauric acid macrogolglycerids, cetyl alcohols, polyglycryle di-isostearate, diethylene glycol monostearate, ethylene monostearate, omega-3 fatty acids, and mixtures thereof,
suppository fatty base, comprising glycerine, triglycerids, theobroma oils, cocoa butter, and mixtures thereof,
mixtures thereof.

Said viscoeslastic compound (iii) is selected from the group comprising:
poly-N-vinylamides,
gums,
fatty alcohols,
poly-N-vinyl-lactams,
polyvinyl alcohols,
polyoxiethylenes,
polyethylene glycols,
polydextroses,
hydrogenated mono-, di- and polysaccharides,
polyvinylpyrrolidones, these being preferred,
and mixtures thereof.

Said plasticizer (iv) is selected from the group comprising:
glycerol, glycerol esters, preferably acetylated glycerides, glycerylmonostearates, glyceryltriacetate, glyceryltributyrate,
phtalates, preferably: dibutylphthalate, diethylphthalate, dimethylphthalate, dioctyl-phthalate,
citrates, preferably: acetyltributylcitrate, acetyltriethylcitrate, tributylcitrate, triethyl-citrate,
sebaçates, preferably: diethylsebacate, dibutylsebacate,
adipates,
azelates,
benzoates,
vegetable oils, preferably: cotton oils, soybean oils, palm oils, castor oils, and mixtures thereof,
fumarates, preferably: diethylfumarate,
malates, preferably: diethylmalate,
oxalates, preferably: diethyloxalate,
succinates; preferably: dibutylsuccinate,
butyrates,
cetyl alcohol esters,
triacetine,
malonates, preferably: diethylmalonate,
and mixtures thereof.

The additive possibly comprised in the anti-crushing agent (a) is preferably selected from the group comprising: compression agents, and/or inert microbeads, and/or gums, and/or viscoelastic compound as defined above.

The viscosity agents, intended to prevent misuse of the analgesic active principle after a possible liquid extraction, aim at increasing the viscosity of the extracted liquid, so as to impair misuse, notably by injection.

The viscosity agents are preferably located in microcapsules containing said viscosity agents, and/or on microcapsules containing the active principle, and/or in a partial or total overcoating of said dosage form, and/or free from said dosage form.

Preferably, said viscosity agent is selected from the group comprising:
  acrylic polyacids and derivatives thereof, and/or
  polyoxyethylenes, and/or
  polyvinyl alcohol, and/or
  polyvinylpyrrolidones, and/or
  gelatins
  cellulose derivatives, for instance hydroxypropylmethylcellulose, methylcellulose, hydroxyethylcellulose, carboxymethylcellulose, hydroxypropylcellulose, and/or
  polysaccharides, preferably from the group comprising sodium alginate, pectins, guar, xanthanes, carraghenanes, gellanes, and/or
  mixtures thereof.

The oral dosage form according to the invention presents at least one of the following remarkable features:
  It cannot, or with difficulty, be transformed into a dry inhalable form;
  It cannot, or with difficulty, be transformed into a liquid injectable form;
  The extraction of the analgesic active principle by chewing is not efficient;
  Moreover, the liquid extraction of the analgesic active principle leads to the complexation of said active principle, thereby rendering it useless by the oral route.

The dosage form according to the invention can comprise, in addition to micro-units made of modified release microcapsules of analgesic active principle, micro-units of analgesic active principle other than microcapsules, among which immediate release micro-granules. Advantageously, said micro-granules are not coated and are of the same type as those used to prepare microcapsules according to the invention.

Advantageously, said analgesic active principle is an opioid active principle, preferably an opioid agonist, in the form of a salt. Preferably, said opioid active principle is selected from the group comprising: anileridine, acetorphine, acetylalphamethylfentanyl, acetyldihydrocodeine, acetylmethadol, alfentanil, allylprodine, alphacetylmethadol, alphameprodine, alphaprodine, alphamethadol, alphamethylfentanyl, alpha-methylthio-fentanyl, alphaprodine, anileridine, atropine, butorphanol, benzethidine, benzylmorphine, beta-hydroxyfentanyl, beta-hydroxy-methyl-3-fentanyl, betacetylmethadol, betameprodine, betamethadol, betaprodine, bezitramide, buprenorphine, butyrate de dioxaphetyl, clonitazene, cyclazocine, cannabis, cetobemidone, clonitazene, codeine, coca, cocaine, codoxime, dezocine, dimenoxadol, dioxaphetylbutyrate, dipipanone, desomorphine, dextromoramide, dextropropoxyphene, diampromide, diethylthiambutene, difenoxine, dihydrocodeine, dihydroetorphine, dihydromorphine, dimenoxadol, dimepheptanol, dimethylthiambutene, diphenoxylate, dipipanone, drotebanol, eptazocine, ethoheptazine, ethylmethylthiambutene, ethylmorphine, etonitazene, ecgonine, ephedrine, ethylmethylthiambutene, ethylmorphine, etonitazene, etorphine, etoxeridine, fentanyl, furethidine, heroïne, hydrocodone, hydromorphinol, hydromorphone, hydroxypethidine, isomethadone, ketobemidone, levallorphane, lofentanil, levomethorphane, levomoramide, levophenacylmorphane, levorphanol, meptazinol, meperidine, metazocine, methadone, methyldesorphine, methyldihydro-morphine, methylphenidate, methyl-3-thiofentanyl, methyl-3-fentanyl, metopon, moramide, morpheridine, morphine, mppp, myrophine, nalbuphine, narceine, nicomorphine, norlevorphanol, normethadone, nalorphine, normorphine, nicocodine, nicodicodine, nicomorphine, noracymethadol, norcodeine, norlevorphanol, normethadone, normorphine, norpipanone, opium, oxycodone, oxymorphone, papavereturn, phenadoxone, phenoperidine, promedol, properidine, propiram, propoxyphene para-fluorofentanyl, pepap, pentazocine, pethidine, phenampromide, phenazocine, phenomorphane, phenoperidine, pholcodine, piminodine, piritramide, proheptazine, propanolol, properidine, propiram, racemethorphane, racemoramide, racemorphane, remifentanil, sufentanil, thebacone, thebaine, thiofentanyl, tilidine, trimeperidine, tramodol, pharmacologically acceptable salts thereof and their mixtures.

The oral dosage forms according to the instant invention can comprise at least one further active principle, distinct from an analgesic active principle. This non-analgesic active principle is preferably selected from the group comprising: anti-depressants amphetamines, anorectics, pain killers, antiepileptics, anitmigraines, antiparkinson agents, antitussives, anxiolytics, barbiturics, benzodiazepines, hypnotiqcs, laxatives, neuroleptics, psychostimulants, psychotropes, sedatives, stimulants, anti-inflammatory agents, the pharmacologically acceptable salts thereof, and their mixtures.

As regards anti-inflammatory active principles, the following can be listed: ibuprofen, acetaminophen, diclofenac, naproxen, benoxaprofen, flurbiprofen, fenoprofen, flubufen, ketoprofen, indoprofen, piroprofen, carprofen, oxaprozine, pramoprofen, muroprofen, trioxaprofen, suprofen, amineoprofen, tiaprofenic acid, fluprofen, bucloxic acid, indomethacine, sulindac, tolmetine, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam or isoxicam, the pharmacologically acceptable salts thereof, and their mixtures.

The dosage form can be a modified release dosage form or a combination of a modified release form and an immediate release form. The active principle can be comprised into modified release microparticles and possibly into immediate release microparticles.

The modified release multiparticulate form of the oral analgesic active principle composition according to the invention, can be:
  a reservoir type form
  and/or a matricial type form.

"Reservoir type form", is intended to denote, in the present disclosure, a form in which the volume of material containing the active principle is entirely coated by at least a film which controls the diffusion release speed of the active principle through the continuous film (or membrane) which does not include the active principle. This release occurs as a result of the contact of the system with the liquid of the gastro intestinal tract. The active principle containing material is, for example, the active principle in itself, a mixture of pharmaceutical additives or a mixture of pharmaceutical additives with the active principle. The reservoir form comprises, for example, a plurality of individually coated microcapsules or a monolithic system such as coated tablet(s), a tablet or any other pharmaceutical form containing a plurality of coated microcapsules.

"Matricial type form" is intended to denote, in the present disclosure, a form in which the analgesic active principle is dispersed in a solid continuous (polymeric) phase (the matrix) that controls the diffusion release speed of the active principle. Said matrix can or cannot be erodable. Said matrix e.g. consists of pharmaceutically acceptable additives known by the man skilled in the art. The matricial type form includes, for instance, a plurality of matricial micro-granules (matricial elements) containing the active principle. These matricial elements are non-coated or partially coated. The matricial type form can be, e.g., also a monolithic system (matricial element), such as a tablet(s) non-entirely coated by at least one continuous film, which does not contain any reservoir form. So, the matricial type form can be, e.g. a tablet containing a plurality of active principle immediate release granules or active principle(s) sustained release granules, said granules being dispersed in a polymeric matrix.

In an embodiment of the invention, the dosage form comprises a plurality of microparticles for the modified release of said analgesic active principle, each microparticles individually comprising a core and a coating on said core. The core comprises at least one analgesic active principle and the coating controls the modified release of said active principle. Preferably, said microparticles have a mean diameter (in volume) lower than or equal to 1,000 μm.

In a first embodiment of the dosage form according to the invention, the modified release form of the analgesic active principle is a sustained release form with an in vitro release profile, such that 70% of the active principle is released over a period of time of between 1 and 24 hours, preferably 2 and 12 hours and even more preferably between 2 and 8 hours.

Advantageously, the composition of the individual coating of the microparticles or the matrix of the microparticles, according to the first embodiment, corresponds to one of the two following families A and B:

Family A
—A1—at least one film-forming polymer (P1) which is insoluble in the fluids of the tract, present in a proportion of 50 to 90%, preferably 50 to 80%, by weight on a dry basis with respect to the total mass of the coating composition and composed of at least one water-insoluble cellulose derivative of cellulose,
—A2—at least one nitrogenous polymer (P2), present in a proportion of 2 to 25%, preferably 5 to 15%, by weight on a dry basis with respect to the total mass of the coating composition and composed of at least one polyacrylamide and/or one poly-N-vinylamide and/or one poly-N-vinyllactam,
—A3—at least one plasticizer, present in a proportion of 2 to 20%, preferably of 4 to 15%, by weight on a dry basis with respect to the total mass of the coating composition and composed of at least one of the following compounds: glycerol esters, phthalates, citrates, sebacates, esters of cetyl alcohol, castor oil, and salicylic acid;
—A4—at least one surface-active and/or lubricating agent, present in a proportion of 2 to 20%, preferably of 4 to 15%, by weight on a dry basis with respect to the total mass of the coating composition and chosen from anionic surfactants, and/or from nonionic surfactants, and/or from lubricating agents, it being possible for said agent to comprise just one or a mixture of products mentioned above.

Family A can be exemplified as follows:
—A1—ethylcellulose and/or cellulose acetate,
—A2—polyacrylamide and/or polyvinylpyrrolidone;
—A3—castor oil,
—A4—alkali metal or alkaline earth metal salts of fatty acids, stearic acid and/or oleic acid being preferred; polyoxyethylenated sorbitan esters and/or polyoxyethylenated castor oil derivatives; stearates, preferably calcium stearate, magnesium stearate, aluminium stearate or zinc stearate.

Family B
—B1—at least one film-forming polymer insoluble in the gastrointestinal tract fluids;
—B2—at least one water-soluble polymer;
—B3—at least one plasticizer;
—B4—optionally at least one surfactant/lubricant preferably comprising at least an anionic surfactant and/or at least a non-ionic surfactant, Family B can be exemplified as follows:
—B1—
water-insoluble cellulose derivatives, ethyl cellulose and/or cellulose acetate being particularly preferred;
acrylic derivatives;
polyvinyl acetates;
and mixtures thereof;
—B2—
water-soluble cellulose derivatives;
polyacrylamides; poly-N-vinylamides;
poly-N-vinyllactams;
polyvinyl alcohols;
polyoxyethylenes;
polyvinylpyrrolidones (the latter being preferred); and mixtures thereof;
—B3—
glycerol and its esters, preferably from the following subgroup: acetylated glycerides, glycerol monostearate, glyceryl triacetate and glycerol tributyrate;
phthalates, preferably from the following subgroup: dibutyl phthalate, diethyl phthalate, dimethyl phthalate and dioctyl phthalate;
citrates, preferably from the following subgroup: acetyltributyl citrate, acetyltriethyl citrate, tributyl citrate and triethyl citrate;
sebacates, preferably from the following subgroup: diethyl sebacate and dibutyl sebacate;
adipates;
azelates;
benzoates;
vegetable oils;
fumarates, preferably diethyl fumarate;
malates, preferably diethyl malate;
oxalates, preferably diethyl oxalate;
succinates, preferably dibutyl succinate;
butyrates;
cetyl alcohol esters;
salicylic acid;
triacetin;
malonates, preferably diethyl malonate;
castor oil (this being particularly preferred);
and mixtures thereof;
—B4—
alkali metal or alkaline earth metal salts of fatty acids, stearic and/or oleic acid being preferred;
polyethoxylated oils, preferably polyethoxylated hydrogenated castor oil;
polyoxyethylene/polyoxypropylene copolymers;
polyethoxylated sorbitan esters;
polyethoxylated castor oil derivatives;
stearates, preferably calcium, magnesium, aluminium or zinc stearate;
stearylfumarates, preferably sodium stearylfumarate;
glycerol behenate;
and mixtures thereof.

Preferably, the coating comprises a single layer, the weight of which represents between 1 and 50%, preferably between 5 and 40%, by weight, of the total weight of said microparticles.

For further details, in particular qualitative and quantitative details, regarding at least some of the constituents of this coating composition, reference will be made, for example, to European patent EP-B-0 709 087 or to PCT applications WO-A-2004/010983 and WO-A-2004/010984, the content of which is integrated into the present disclosure by way of reference.

According to a second embodiment of the solid oral dosage form according to the invention, the modified release solid oral dosage form of analgesic is a sustained release form with an in vitro dissolution behaviour such that:

the release of analgesic is controlled by means of two distinct triggering mechanisms, one being based on a variation in pH and the other allowing the release of the active principle(s) after a predetermined period of residence in the stomach;

at constant pH 1.4, the dissolution profile comprises a lag phase of less than or equal to 7 hours, preferably less than or equal to 5 hours, and even more preferably of between 0.25 and 5 hours;

and the change from pH 1.4 to pH 7.0 results in a release phase that begins without any lag time.

More preferably, the modified release solid oral dosage form according to this second embodiment has an in vitro dissolution behaviour, measured in an in vitro dissolution test, such that:

less than 20% of the analgesic is released after 2 h at pH 1.4;

at least 50% by weight of the analgesic is released after 16 h at pH 1.4.

According to the second embodiment of the invention, the analgesic active principle is released in vitro according to a double trigger mechanism, from microparticles containing said active principle. The coating or the matrix for modified release of the active principle comprises:

at least one hydrophilic polymer (I) carrying groups that are ionized at neutral pH, at least one hydrophobic compound (II);

the mean diameter of said microparticles is less than 2000 µm, and preferably between 50 and 800 µm, and even more preferably between 100 and 600 µm.

According to another advantageous characteristic, the composite material I-II for the coating for modified release of the active principle with low solubility is such that:

the II/I weight ratio is between 0.2 and 1.5, preferably between 0.5 and 1.0, and the hydrophobic compound II is selected from products that are crystalline in the solid state and that have a melting point MpB≥40° C., preferably MpB≥50° C., and even more preferably 40° C.≤MpB≤90° C.

According to a species of predilection, the hydrophilic polymer (I) is chosen from:

I.a copolymers of (meth)acrylic acid and of (meth)acrylic acid alkyl ester, and mixtures thereof, I.b cellulose derivatives, preferably cellulose acetates, cellulose phthalates, cellulose succinates and mixtures thereof, and even more preferably hydroxypropylmethylcellulose phthalates, hydroxypropylmethylcellulose acetates, hydroxypropylmethylcellulose succinates and mixtures thereof;

and mixtures thereof.

The polymers (I) that are even more preferred are copolymers of (meth)acrylic acid and of (meth)acrylic acid alkyl (e.g. $C_1$-$C_6$ alkyl) esters. These copolymers are, for example, of the type of those sold by the company Rohm Pharma Polymers under the registered trade marks EUDRAGIT®, series L and S (such as, for example, EUDRAGIT® L100, S100, L30 D-55 and L100-55). These copolymers are anionic enteric copolymers that are soluble in aqueous medium at pHs above those encountered in the stomach.

Still according to the embodiment of predilection, the compound (II) is chosen from the group of products below:

II.a plant waxes taken on their own or as mixtures with one another;

II.b hydrogenated plant oils taken on their own or as mixtures with one another;

II.c mono- and/or di- and/or triesters of glycerol and of at least one fatty acid;

II.d mixtures of monoesters, of diesters and of triesters of glycerol and of at least one fatty acid;

and mixtures thereof.

Even more preferably, the compound (II) is chosen from the group of following products:

hydrogenated cottonseed oil, hydrogenated soybean seed oil, hydrogenated palm oil, glyceryl behenate, hydrogenated castor oil, tristearin, tripalmitin, trimyristin, yellow wax, hard fat or fat that is useful as suppository bases, anhydrous dairy fats, lanolin, glyceryl palmitostearate, glyceryl stearate, lauryl macrogolglycerides, cetyl alcohol, polyglyceryl diisostearate, diethylene glycol monostearate, ethylene glycol monostearate, omega-3 and any mixture thereof, preferably from the subgroup of following products: hydrogenated cottonseed oil, hydrogenated soybean seed oil, hydrogenated palm oil, glyceryl behenate, hydrogenated castor oil, tristearin, tripalmitin, trimyristin and any mixture thereof.

In practice, and without this being limiting, it is preferable for the compound (II) to be chosen:

from the group of products sold under the following trade marks: Dynasan®, Cutina®, Hydrobase®, Dub®, Castorwax®, Croduret®, Compritol®, Sterotex®, Lubritab®, Apifil®, Akofine®, Softtisan®, Hydrocote®, Livopol®, Super Hartolan®, MGLA®, Corona®, Protalan®, Akosoft®, Akosol®, Cremao®, Massupol®, Novata®, Suppocire®, Wecobee®, Witepsol®, Lanolin®, Incromega®, Estaram®, Suppoweiss®, Gelucire®, Precirol®, Emulcire®, Plurol diisostéarique®, Geleol®, Hydrine® and Monthyle®, and mixtures thereof, and also from the group of additives for which the codes are as follows: E 901, E 907, E 903 and mixtures thereof, and, preferably, from the group of products sold under the following trade marks: Dynasan® P60, Dynasan® 114, Dynasan® 116, Dynasan® 118, Cutina® HR, Hydrobase® 66-68, Dub® HPH, Compritol® 888, Sterotex® NF, Sterotex® K, Lubritab® and mixtures thereof.

According to another advantageous characteristic of this embodiment, the coating for modified release of the active principle is free of talc.

For further details regarding the preparation of these microparticles according to this embodiment, in particular in their embodiment with a neutral core coated with at least one active layer comprising active principle(s) and with at least one outer coating for modified release of the active principle(s), reference will be made to the content of PCT application WO-A-FR03/030878, the content of which is integrated into the present disclosure by way of reference.

According to a third embodiment of the invention, the dosage form comprises at least two different populations of microparticles. Each population of modified release microparticles can correspond either to the first embodiment, or the second embodiment as disclosed above.

According to a fourth embodiment of the invention, the dosage form comprises an immediate release microparticles population and at least one modified release microparticles population.

The above-mentioned coated microparticles may have different structures. According to a first structure, some of the microparticles comprise a core containing the active principle and a coating over the core, said coating allowing the modified release of the active principle.

According to a second structure, some of the microparticles comprise a core containing a neutral core and at least a layer containing the active principle and coating the neutral core, said microparticle further containing a coating over the core, said coating allowing the modified release of the active principle.

Preferably, in the dosage form according to the invention, the antimisuse agent is located:
in microparticles containing said antimisuse agent, and/or
in a matrix containing said analgesic active principle, and/or
in a coating of microparticles containing said analgesic active principle, and/or
in a partial or total over-coating of said dosage form, and/or
free from said dosage form.

As regards the microparticles containing the quenching agent, they can be coated with a film coating, the composition of which is chosen amongst families A and B as disclosed above (first embodiment of the dosage form containing the analgesic active principle).

These microparticles containing the quenching agent release the quenching agent with an in vitro release profile such that, for example, 70% of the quenching agent is released for a period of time between 1 and 24 h, preferably 2 and 12 h, more preferably 2 and 8 h.

The microparticles containing the quenching agent release the quenching agent can also be coated with a coating as disclosed for the second embodiment mentioned above. The quenching agent is released, for example, with an in vitro release profile with an in vitro dissolution behavior such that:
the release of the quenching agent is controlled by means of two distinct triggering mechanisms, one being based on a variation in pH and the other allowing the release of the active principle(s) after a predetermined period of residence in the stomach;
at constant pH 1.4, the dissolution profile comprises a lag phase of less than or equal to 7 hours, preferably less than or equal to 5 hours, and even more preferably of between 0.25 and 5 hours;
and the change from pH 1.4 to pH 7.0 results in a release phase that begins without any lag time.

More preferably, the modified release solid oral dosage form according to this second embodiment has an in vitro dissolution behavior, measured in an in vitro dissolution test, such that for example:
less than 20% of the quenching agent is released after 2 h at pH 1.4;
at least 50% by weight of the quenching agent is released after 16 h at pH 1.4.

Advantageously, these dosage forms, novel in their structure, their presentation and their composition, are presented in the form of a tablet, a sachet of powder, a sachet of a powder for multidose suspension to be reconstituted, a tablet or a gelatin capsule.

EXAMPLES

Example 1

Oxycodone Misuse Resistive Capsule

Step 1:
600 g of Oxycodone HCl and 60 g of Klucel EF® (Hydroxypropyl cellulose/Aqualon) are dissolved in 5000 g of water. The solution is sprayed onto 300 g of neutral microspheres (Asahi-Kasei) in a GPCG1 Glatt spray coater. 35 g of ethyl cellulose (Ethocel 20 Premium/Dow), 5 g of Plasdone K29/32® (Povidone/ISP), 2.5 g of Cremophor RH 40 (Macrogolglyceroli hydroxystearas/BASF) and 7.5 g of castor oil are dispersed in a 60% isopropanol and 40% acetone mixture. This solution is sprayed onto 350 g of Oxycodone granules previously prepared.
Step 2:
550 g of sodium dodecylsulfate (SDS) and 50 g of Klucel EF® (Hydroxypropyl cellulose/Aqualon) are dispersed in 3000 g of ethanol. The solution is sprayed onto 250 g of neutral microspheres (Asahi-Kasei) in a GPCG1 Glatt spray coater. 30 g of HPMC (Hypromellose K15MP/Dow), 10 g of Plasdone K29/32® (Povidone/ISP), 2.5 g of Cremophor RH 40 (Macrogolglyceroli hydroxystearas/BASF) and 7.5 g of castor oil are dipersed in a 60% isopropanol and 40% acetone mixture. This solution is sprayed onto 450 g of SDS granules previously prepared.
Step 3
146 mg of micro-particles obtained in step 1 are mixed with 105 mg of micro-particles obtained in step 2 and put in a size 1 gelatin hard capsule.
If the capsule is broken and emptied in a glass of water a precipitate containing the Oxycodone is obtained.

Example 2

Quenching of Oxycodone Hydrochloride by Sodium Dodecylsulfate in Water

In example 2, two solutions were prepared. Solution A is Oxycodone hydrochloride at 5 g/L in tap water. Solution B is SDS (sodium dodecylsufate) at 5 g/L in tap water.

Solution A is added to solution B. The resulting soution A+B is turbid. After a few minutes, a complex containing the oxycodone precipitates. This complex remains stable even if diluted in a larger amount of tap water (more than 2 times).

Therefore, oxycodone cannot be misused, either by oral administration or by injection of a concentrated solution.

Example 3

Oxycodone Misuse Resistive Capsules

Step 1: Granule
1615 g oxycodone and 85 g Povidone (Plasdone® K29-32/ISP) were dispersed in 60:40 v/v water/ethanol. This solution was sprayed over 300 g of cellulose spheres (Asahi-Kasei) in a fluid bed coater (Glatt GPCG1).

Step 2: Anti-Crushing Microparticles 315 g ethylcellulose (Ethocel 20 Premium/Dow), 81 g de povidone (Plasdone K29-32/ISP), 18 g de Macrogolglyceroli hydroxystearas (Cremophor RH40/BASF) and 36 g castor oil (Garbit Huilerie) are dissolved in 60:40 v/v acetone/isopropanol. This solution is sprayed over 450 g granules obtained from step 1.

Figure 1:
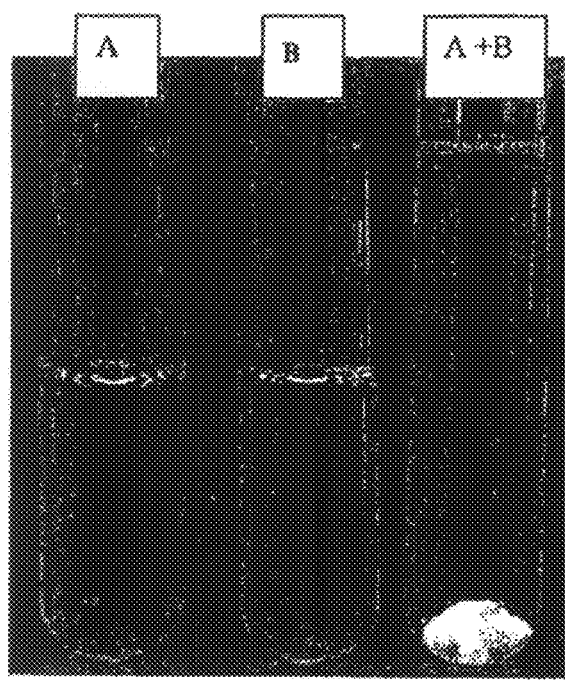
FIG. 1 illustrates example 2. It is a picture of the solutions obtained as follows:
A: Solution A is oxycodone HCl at 5 g/L in water
B: Solution B is SDS at 5 g/L in water
A+B: Solution A and B mixed, a precipitate entrapping the oxycodone is formed
Figure 2:
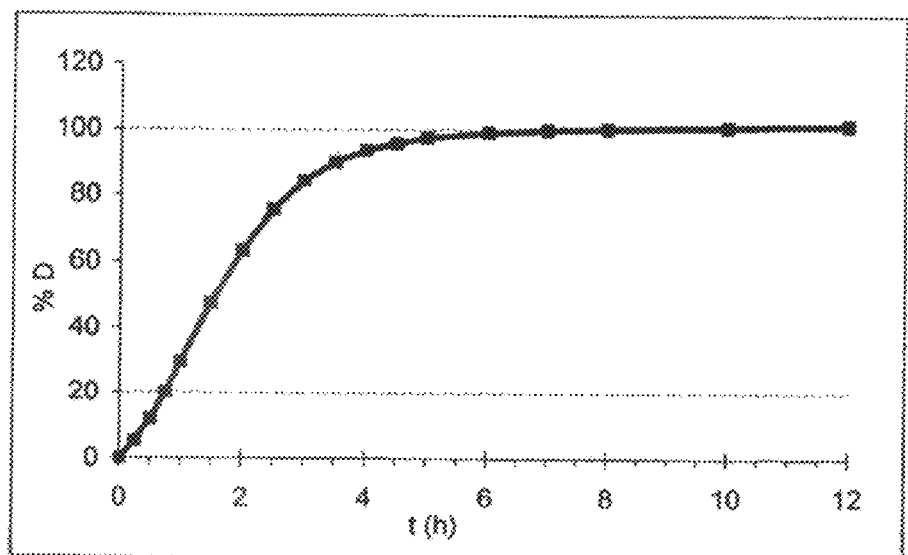
FIG. 2 illustrates the in vitro dissolution profile of microparticles of example 3 in a reference test (% AP dissolved v. time)

The coating whose mass is 50 wt % of the total mass of the coated microparticles, leads to the dissolution profile of FIG. 2. The dissolution test is performed according to the reference dissolution test.

Example 4

Oxycodone Misuse Resistive Capsule 230 mg microparticles obtained from step 2 of Example 3, 100 mg of crushed and sieved Amberlite IR69F (sodium polystyrene sulfonate), 70 mg sieved Polyox WSR 303 Sentry (polyethylene oxyde), 3.8 mg magnesium stearate and 1.9 mg d'Aerosil 200 (colloidal silica) are filled in a size 0 gelatin capsule.

This oxycodone capsule is protected against misuse.

Figure 3A:
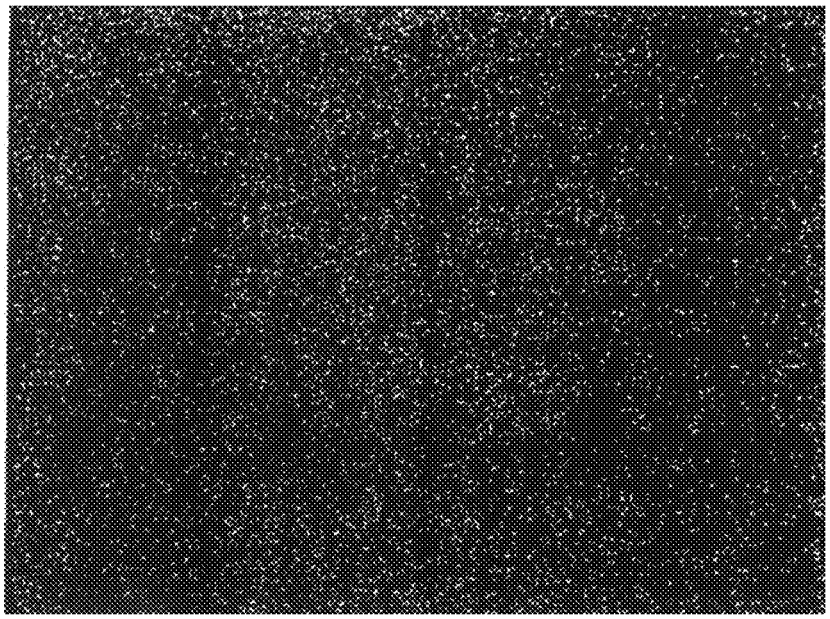
FIG. 3 shows a picture of the content of a capsule according to example 4, by the naked eye (A) and with an optical microscope (B).
Figure 3B:
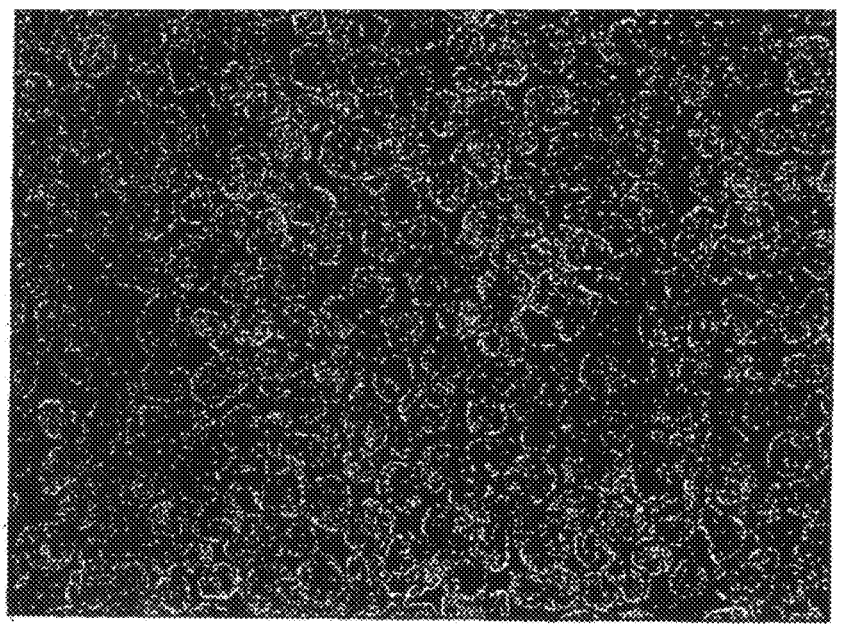

As shown in FIG. 3A (naked eye) and 3B (optical microscope), AP microparticles and viscosity agent microparticles cannot be distinguished and cannot be sieved.

We claim:

1. An oral solid dosage form comprising:
(a) at least one salt of at least one analgesic active principle,
(b) an anti-misuse system comprising at least one quenching agent,
said dosage form comprising a first population of microparticles for the modified release of said analgesic active principle, each microparticle of the first population of microparticles individually comprising (1) a core comprising said at least one analgesic active principle salt, and (2) a coating on said core, wherein the coating controls the modified release of said analgesic active principle, wherein said first population of microparticles is in a non-complexed form relative to said quenching agent,
said dosage form further comprising a second population of microparticles containing said quenching agent,
wherein said quenching agent is a salt comprising ion having the opposite polarity to the polarity of the analgesic active principle salt in solution,
wherein said quenching agent comprises a salt of an ion exchange resin or a salt selected from the group consisting of:
sodium dodecyl sulfate, sodium docusate, anionic methacrylic copolymers, methyl methacrylate and methacrylic acid copolymers, crosslinked acrylic polyacids, carboxymethylcelluloses, carboxymethycellulose derivatives, crosslinked carboxymethylcellulose, crosslinked carboxymethylcellulose derivatives, alginates, xanthane, arabic gum, alginate (sulfonate)propylene glycol, glucuronates, carbonates, gluconates, succinates, phosphates, glycerophosphates, lactates, trisilicates, fumarates, adipates, benzoates, tartrates, sulfonamides, acesulfames, metallic salts of Ca, metallic salts of Fe, metallic salts of Mg, metallic salts of Zn, trimethyl tetradecyl ammonium bromide, benzethonium chloride, chitosan, cationic methacrylic copolymers, Eudragit™ RS, Eudragit™ RL, copolymer based on dimethylaminoethyl methacrylate and neutral methacrylic esters and mixtures thereof,
wherein said salt comprises an ion capable of forming a complex with said analgesic active principle salt when said analgesic active principle salt is extracted in vitro in solution, wherein said complex is poorly soluble in common solvents selected from the group of water-ethanol mixtures, alcohol, alcoholic beverages, sodas, vinegar, hydrogen peroxide, and mixtures thereof.

2. The dosage form according to claim 1, wherein the analgesic active principle has a desired pharmacological effect, and the desired pharmacological effect of the analgesic active principle is not impaired by the quenching agent when the dosage form is extracted in vivo.

3. The dosage form according to claim 1, wherein the quenching agent is a cation exchange resin, wherein the cation is selected from the group consisting of: $H^+$, a metallic cation, and $NH_4^+$.

4. The dosage form according to claim 1, wherein the quenching agent is a salt of an ion exchange resin.

5. The dosage form according to claim 1, wherein the quenching agent is selected from the group consisting of:
sodium dodecyl sulfate, sodium docusate, trimethyl tetradecyl ammonium bromide, benzethonium chloride, strong acid cation exchange resins, and strongly alkaline anion exchange resins.

6. The dosage form according to claim 4, wherein said ion exchange resin is a strong acid cation exchange resin and the analgesic active principle is cationic in solution.

7. The dosage form according to claim 4, wherein said ion exchange resin comprises a sulphonated styrene-divinylbenzene copolymer.

8. The dosage form according to claim 4, wherein said ion exchange resin is derived from a styrene-divinylbenzene copolymer bearing quaternary ammonium moieties, or salts thereof.

9. The dosage form according to claim 1, wherein the dosage form comprises modified release microparticles of said quenching agent.

10. The dosage form according to claim 1, wherein said modified release microparticles of analgesic active principle comprise microparticles selected from the group consisting of: sustained release microparticles, delayed release microparticles, pulsed release microparticles, and mixtures thereof.

11. The dosage form according to claim 1, further comprising one or more further antimisuse agents.

12. The dosage form according to claim 11, wherein at least one of said further antimisuse agents comprises at least one anti-crushing agent.

13. The dosage form according to claims 11 or 12, wherein at least one of said further antimisuse agents comprises at least one viscosity agent.

14. The dosage form according to claim 11, wherein the one or more further antimisuse agents are located:
in microparticles containing said antimisuse agent; in a matrix containing said analgesic active principle and said antimisuse agent; in a coating of microparticles containing said analgesic active principle; in a partial or total overcoating of said dosage form; or free from said dosage form.

15. The dosage form according to claim 12, wherein said anti-crushing agent comprises:
(a) an overcoating on said microparticles of analgesic active principle, said overcoating having at least one of the following features:
(i) viscoelastic properties, to absorb the energy dissipated during crushing;

(ii) a low cohesivity, to favour breaking of the overcoating rather than breaking of the microparticles during crushing;

(iii) a low surface energy, to favour gliding of the microparticles one on the other during crushing;

(iv) an ability to form a paste under high shear;

(b) one or more free additives, wherein said additives are capable of partially or completely preventing the crushing of the dosage form comprising said analgesic active principle; or (c) both an overcoating and one or more free additives.

16. The dosage form according to claim 15, wherein said overcoating comprises:

(i) at least one film-forming polymer; and (ii) at least one of the following compounds: a lubricant or lump agent; a viscoelastic compound; and a plasticizer.

17. The dosage form according to claim 16, wherein said film-forming polymer is selected from the group consisting of cellulose-based compounds, acrylic polymers, and mixtures thereof.

18. The dosage form according to claim 16, wherein said lubricant or lump agent is selected from the group consisting of:

stearic acid, stearates, magnesium oxide, poloxamers, sodium benzoate, anionic surfactants, cationic surfactants, non ionic surfactants, starch, talc, colloidal silica, waxes, hydrogenated vegetable oils, glycerol behenate, castor hydrogenated oils, tristearines, tripalmitines, trimyristines, hard fat, dairy anhydrous fat, lanolins, lauric acid macrogolglycerids, cetyl alcohols, omega-3 fatty acids, suppository fatty base, and mixtures thereof.

19. The dosage form according to claim 16, wherein said viscoeslastic compound is selected from the group consisting of:

poly-N-vinylamides, gums, fatty alcohols, poly-N-vinyllactams, polyvinyl alcohols, polyoxiethylenes, polyethylene glycols, polydextroses, hydrogenated monosaccharides, hydrogenated disaccharides, hydrogenated polysaccharides, polyvinylpyrrolidones, and mixtures thereof.

20. The dosage form according to claim 16, wherein said plasticizer (iv) is selected from the group consisting of:

glycerol, glycerol esters, phthalates, citrates, sebaceates, adipates, azelates, benzoates, vegetable oils, fumarates, malates, oxalates, succinates, butyrates, cetyl alcohol esters, malonates, and mixtures thereof.

21. The dosage form according to claim 15, wherein said additive is selected from the group consisting of:

compression agents, inert microbeads, gums, a viscoelastic compound, and combinations thereof.

22. The dosage form according to claim 13, wherein the viscosity agent is capable of increasing the viscosity of an in vitro extracted liquid prepared from said dosage form.

23. The dosage form according to claim 22, wherein said viscosity agent is selected from the group consisting of:

acrylic polyacids, derivatives of acrylic polyacids, polyoxyethylenes, polyvinyl alcohol, polyvinylpyrrolidones, gelatins, cellulose-based compounds, polysaccharides, and mixtures thereof.

24. The dosage form according to claim 1, wherein said microparticles for the modified release of said analgesic active principle have a mean diameter lower than or equal to 1,000 μm.

25. The dosage form according to claim 1, wherein said analgesic active principle comprises an opioid active principle in the form of a salt.

26. The dosage form according to claim 25, wherein said opioid active principle is selected from the group consisting of:

acetorphine, acetylalphamethylfentanyl, acetyldihydrocodeine, acetylmethadol, alfentanil, allylprodine, alphacetylmethadol, alphameprodine, alphaprodine, alphamethadol, alphamethylfentanyl, alpha-methylthiofentanyl, anileridine, atropine, butorphanol, benzethidine, benzylmorphine, beta-hydroxyfentanyl, beta-hydroxy-methyl-3-fentanyl, betacetylmethadol, betameprodine, betamethadol, betaprodine, bezitramide, buprenorphine, clonitazene, cyclazocine, cannabis, codeine, coca, cocaine, codoxime, dezocine, dimenoxadol, dioxaphetylbutyrate, desomorphine, dextromoramide, dextropropoxyphene, diampromide, diethyl-thiambutene, difenoxine, dihydrocodeine, dihydroetorphine, dihydromorphine, dimenoxadol, dimepheptanol, dimethylthiambutene, diphenoxylate, dipipanone, drotebanol, eptazocine, ethoheptazine, ethylmethylthiambutene, ethylmorphine, etonitazene, ecgonine, ephedrine, ethylmethylthiambutene, ethylmorphine, etorphine, etoxeridine, fentanyl, furethidine, heroine, hydrocodone, hydromorphone, hydromorphinol, hydromorphone, hydroxypethidine, isomethadone, ketobemidone, levallorphane, lofentanil, levomethorphane, levomoramide, levophenacylmorphane, levorphanol, meptazinol, meperidine, metazocine, methadone, methyldesorphine, methyldihydro-morphine, methylphenidate, methyl-3-thiofentanyl, methyl-3-fentanyl, metopon, moramide, morpheridine, morphine, mppp, myrophine, nalbuphine, narceine, norlevorphanol, normethadone, nalorphine, normorphine, nicocodine, nicodicodine, nicomorphine, noracymethadol, norcodeine, norpipanone, opium, oxycodone, oxymorphone, papavereturn, phenadoxone, phenoperidine, promedol, propoxyphene para-fluorofentanyl, pepap, pentazocine, pethidine, phenampromide, phenazocine, phenomorphane, phenoperidine, pholcodine, piminodine, piritramide, proheptazine, propanolol, properidine, propiram, racemethorphane, racemoramide, racemorphane, remifentanil, sufentanil, thebacone, thebaine, thiofentanyl, tilidine, trimeperidine, tramadol, pharmacologically acceptable salts thereof and their mixtures.

27. The dosage form according to claims 1, 25, or 26, comprising at least one non-analgesic active principle selected from the group consisting of:

anti-depressants, amphetamines, anorectics, pain killers, antiepileptics, antimigraines, antiparkinson agents, antitussives, anxiolytics, barbiturics, benzodiazepines, hypnotics, laxatives, neuroleptics, psychostimulants, psychotropes, sedatives, stimulants, anti-inflammatory agents, the pharmacologically acceptable salts thereof, and combinations thereof.

28. The dosage form according to claim 1, wherein the dosage form is in the form of tablets, powders, sachets, or capsules.

29. The dosage form according to claim 4, wherein said ion exchange resin is a strong alkali anion exchange resin and the analgesic active principle is anionic in solution.

30. An oral solid dosage form comprising at least one salt of at least one analgesic active principle, said dosage form comprising a first population of microparticles for the modified release of said analgesic active principle salt, some of the microparticles of said first population of microparticles individually comprising (1) a core comprising said at least one analgesic active principle salt, and (2) a coating on said core, said coating allowing the modified release of said analgesic active principle, said dosage form further comprising a second population of microparticles containing said quenching agent, in a non-complexed form with said analgesic active principle salt within the oral solid dosage form, wherein said quenching agent is chosen from the group consisting of:

sodium dodecyl sulfate, sodium docusate, trimethyl tetradecyl ammonium bromide, benzethonium chloride, strong acid cation exchange resin and strong alkali anion exchange resin, and mixtures thereof.

31. The dosage form according to claim 30, wherein said cation exchange resin comprises a sulphonated styrene-divinylbenzene copolymer.

32. The dosage form according to claim 30, wherein said anion exchange resin is a styrene-divinylbenzene copolymer bearing quaternary ammonium moieties.

33. The dosage form according to claim 30, wherein said analgesic active principle is an opioid.

34. The dosage form according to claim 33, wherein said opioid is selected from the group consisting of: oxycodone, oxymorphone, hydromorphone, hydrocodone, tramadol, morphine, buprenorphine, dextropropoxyphene, propoxyphene, codeine, fentanyl, alfentanyl, remifentanyl, methadone, pethydine, nalbuphine, levomethadyl acetate, difenoxine, diphenoxylate, loperamide, pentazocine, butorphanol, levorphanol, tapentadol and their pharmaceutically acceptable salts, polymorphs and solvates.

35. The dosage form according to claim 33, wherein said opioid is selected from the group consisting of: oxycodone hydrochloride, hydromorphone hydrochloride or morphine sulphate.

36. The dosage form according to claim 1 or 30, wherein:
the analgesic active principle is oxycodone hydrochloride, and
the quenching agent is sodium dodecyl sulfate.

37. The dosage form according to claim 36, wherein:
the coating of the oxycodone modified release microparticles comprises 70% ethylcellulose, 10% povidone, 5% macrogolglyceroli hydroxystearate and 15% castor oil; and
the microparticles of sodium dodecyl sulfate comprise a core containing sodium dodecyl sulfate and a coating comprising 60% hydrxopropyl methylcellulose, 20% povidone, 5% macrogolglyceroli hydroxystearate and 15% castor oil.

38. The dosage form according to claim 1 or 30, wherein:
the analgesic active principle is oxycodone hydrochloride, and
the quenching agent is sodium polystyrene sulfonate.

39. The dosage form according to claim 38, which further comprises polyethylene oxide microparticles distinct from the oxycodone modified release microparticles.

40. The dosage form according to claim 38, wherein the coating of the oxycodone modified release microparticles comprises 70% ethylcellulose, 18% povidone, 4% macrogolglyceroli hydroxystearate and 8% castor oil.

41. The dosage form according to claim 38, wherein the coating of the oxycodone modified release microparticles has a mass representing 50 wt % of the total mass of the coated oxycodone microparticles.

42. The dosage form according to claim 9, wherein said modified release microparticles of quenching agent comprise microparticles selected from the group consisting of: sustained release microparticles, delayed release microparticles, pulsed release microparticles, and mixtures thereof.

* * * * *